(12) United States Patent
Barrow-Williams et al.

(10) Patent No.: US 8,313,463 B2
(45) Date of Patent: Nov. 20, 2012

(54) INJECTION DEVICE

(75) Inventors: Tim Barrow-Williams, Melbourn (GB);
Rosemary Habeshaw, Melbourn (GB)

(73) Assignee: Cilag GmbH International (CH)

( * ) Notice: Subject to any disclaimer, the term of this patent is extended or adjusted under 35 U.S.C. 154(b) by 527 days.

(21) Appl. No.: 11/579,559

(22) PCT Filed: May 27, 2005

(86) PCT No.: PCT/GB2005/002126
§ 371 (c)(1),
(2), (4) Date: Aug. 27, 2008

(87) PCT Pub. No.: WO2005/115510
PCT Pub. Date: Dec. 8, 2005

(65) Prior Publication Data
US 2008/0312590 A1    Dec. 18, 2008

(30) Foreign Application Priority Data

May 28, 2004 (GB) .................................. 0412055.6

(51) Int. Cl.
*A61M 5/20* (2006.01)
(52) U.S. Cl. ........................................ 604/134; 604/157
(58) Field of Classification Search .................. 604/187, 604/68, 235, 156–157, 134, 136, 198, 69–72, 604/45
See application file for complete search history.

(56) References Cited

U.S. PATENT DOCUMENTS

| 1,845,036 A | 2/1932 | Busher |
| 2,019,382 A | 10/1935 | Aronson |
| 2,531,267 A | 11/1950 | Harisch |
| 2,764,977 A | 10/1956 | Ferguson |

(Continued)

FOREIGN PATENT DOCUMENTS

CH    518102 A    1/1972
(Continued)

OTHER PUBLICATIONS

European Search Report dated Aug. 3, 2011; U.S. Appl. No. 11/170,040.
(Continued)

*Primary Examiner* — Nicholas Lucchesi
*Assistant Examiner* — Weng Lee (57) ABSTRACT

An injection device 110 is described having a housing 112 that receives a syringe 114. The syringe 114 is biased by a return spring 126 from an extended position in which the needle 118 extends from the housing 112 through an exit aperture 128 to a retracted position in which it does not. A drive spring 130 acts via a drive to advance the syringe 114 from its retracted position to its extended position and discharge its contents through the needle 118 and a return spring 126, brought into play when the drive has reached a nominal return position, restores the syringe 114 to its retracted position. A releasable locking mechanism retains the syringe 114 in its retracted position. A sleeve 119 projects from the exit aperture 128 and can be depressed to release the locking mechanism. A trigger 300 has a rest position, in which it engages the drive, retaining it in a position corresponding to the retracted position of the syringe 114, and a depressed position, in which it no longer causes the drive to be so retained. The sleeve 119 normally locks the trigger 300 in its rest position. However, depression of the sleeve 119 into the exit aperture 128, allows the trigger to be depressed. Thereafter, the trigger 300 is retained in its active position.

7 Claims, 4 Drawing Sheets

U.S. PATENT DOCUMENTS

| | | |
|---|---|---|
| 2,828,742 A | 4/1958 | Ashkenaz |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,744,786 A | 5/1988 | Hooven et al. |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A | 6/1992 | Lucas |
| 5,137,516 A | 8/1992 | Rand et al. |
| 5,141,496 A * | 8/1992 | Dalto et al. .................. 604/117 |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A | 5/1996 | Knauer |
| 5,520,653 A | 5/1996 | Reilly et al. |
| 5,540,660 A | 7/1996 | Jenson et al. |
| 5,540,709 A | 7/1996 | Ramel |
| 5,567,160 A | 10/1996 | Massino |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,709,662 A | 1/1998 | Olive et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A | 1/2000 | Hitchins et al. |
| 6,036,675 A * | 3/2000 | Thorne et al. .................. 604/232 |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross et al. |
| 6,159,181 A | 12/2000 | Crossman et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 | 9/2001 | Safabash et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |

| | | | | | | |
|---|---|---|---|---|---|---|
| 6,699,220 B2 | 3/2004 | Rolfe | | 2005/0027255 A1 | 2/2005 | Lavi et al. |
| 6,740,062 B2 | 5/2004 | Hjertman | | 2005/0033234 A1 | 2/2005 | Sadowski et al. |
| 6,743,199 B2 | 6/2004 | Shue et al. | | 2005/0049550 A1 | 3/2005 | Kirchhofer et al. |
| 6,743,203 B1 | 6/2004 | Pickhard | | 2005/0049561 A1 | 3/2005 | Hommann et al. |
| 6,746,429 B2 | 6/2004 | Sadowski et al. | | 2005/0075608 A1 | 4/2005 | Holdgate et al. |
| 6,767,336 B1 | 7/2004 | Kaplan | | 2005/0085776 A1 | 4/2005 | Hommann et al. |
| 6,770,056 B2 | 8/2004 | Price et al. | | 2005/0090782 A1 | 4/2005 | Marshall et al. |
| 6,776,777 B2 | 8/2004 | Barelle | | 2005/0101919 A1 | 5/2005 | Brunnberg |
| 6,783,509 B1 | 8/2004 | Landau et al. | | 2005/0124940 A1 | 6/2005 | Martin et al. |
| 6,793,161 B1 | 9/2004 | Fujia et al. | | 2005/0125019 A1 | 6/2005 | Kudna et al. |
| 6,796,967 B2 | 9/2004 | Jensen | | 2005/0137523 A1 | 6/2005 | Wyatt et al. |
| 6,811,548 B2 | 11/2004 | Jeffrey | | 2005/0203466 A1 | 9/2005 | Hommann et al. |
| 6,846,303 B2 | 1/2005 | Eakins et al. | | 2005/0215941 A1 | 9/2005 | Bernard et al. |
| 6,890,319 B1 | 5/2005 | Crocker | | 2005/0215951 A1 | 9/2005 | Saulenas et al. |
| 6,899,698 B2 | 5/2005 | Sams | | 2005/0222539 A1 | 10/2005 | Gonzales et al. |
| 6,932,793 B1 | 8/2005 | Marshall et al. | | 2005/0261633 A1 | 11/2005 | Khalaj |
| 6,939,319 B1 * | 9/2005 | Anstead et al. ........... 604/68 | | 2005/0261634 A1 | 11/2005 | Karlsson |
| 6,979,316 B1 | 12/2005 | Rubin et al. | | 2005/0273054 A1 | 12/2005 | Asch |
| 7,066,907 B2 | 6/2006 | Crossman et al. | | 2005/0273055 A1 | 12/2005 | Harrison et al. |
| 7,097,634 B2 | 8/2006 | Gilbert | | 2005/0277885 A1 | 12/2005 | Scherer |
| 7,118,553 B2 | 10/2006 | Scherer | | 2005/0277886 A1 | 12/2005 | Hommann et al. |
| 7,156,823 B2 | 1/2007 | Landau et al. | | 2005/0277896 A1 | 12/2005 | Messerli et al. |
| 7,744,561 B2 | 6/2010 | Stamp | | 2005/0288633 A1 | 12/2005 | Jeffrey |
| 2001/0005781 A1 | 6/2001 | Bergens et al. | | 2006/0030819 A1 | 2/2006 | Young et al. |
| 2001/0021828 A1 | 9/2001 | Fischer et al. | | 2006/0036216 A1 | 2/2006 | Rimlinger et al. |
| 2001/0037087 A1 * | 11/2001 | Knauer ........... 604/137 | | 2006/0036217 A1 | 2/2006 | Doyle |
| 2001/0037089 A1 | 11/2001 | Domici, Jr. | | 2006/0069345 A1 | 3/2006 | Anderson et al. |
| 2001/0049496 A1 | 12/2001 | Kirchhofer et al. | | 2006/0069348 A1 | 3/2006 | Parker et al. |
| 2002/0072709 A1 | 6/2002 | Sadowski et al. | | 2006/0069350 A1 | 3/2006 | Buenger et al. |
| 2002/0095120 A1 | 7/2002 | Larsen et al. | | 2006/0079834 A1 | 4/2006 | Tennican et al. |
| 2002/0151839 A1 | 10/2002 | Landau | | 2006/0100588 A1 | 5/2006 | Brunnberg et al. |
| 2002/0161334 A1 | 10/2002 | Castellano et al. | | 2006/0106295 A1 | 5/2006 | Jais et al. |
| 2002/0173752 A1 | 11/2002 | Polzin | | 2006/0161111 A1 | 7/2006 | Potter et al. |
| 2002/0183690 A1 | 12/2002 | Arnisolle | | 2006/0178631 A1 | 8/2006 | Gillespie et al. |
| 2003/0036679 A1 | 2/2003 | Kortenbach | | 2006/0178642 A1 | 8/2006 | Gillespie et al. |
| 2003/0036725 A1 | 2/2003 | Lavi et al. | | 2006/0184137 A1 | 8/2006 | Reynolds |
| 2003/0050609 A1 | 3/2003 | Sams | | 2006/0224124 A1 | 10/2006 | Scherer |
| 2003/0060773 A1 | 3/2003 | Nguyen | | 2006/0258986 A1 | 11/2006 | Hunter et al. |
| 2003/0065286 A1 | 4/2003 | Landau | | 2006/0258990 A1 | 11/2006 | Weber |
| 2003/0078546 A1 | 4/2003 | Jensen | | 2006/0270986 A1 | 11/2006 | Hommann et al. |
| 2003/0088207 A1 | 5/2003 | Rogatchev et al. | | 2007/0027430 A1 | 2/2007 | Hommann |
| 2003/0088216 A1 | 5/2003 | Py | | 2007/0078382 A1 | 4/2007 | Hommann et al. |
| 2003/0093030 A1 | 5/2003 | Landau | | 2007/0142787 A1 | 6/2007 | Scherer |
| 2003/0093035 A1 | 5/2003 | Mohammed | | 2008/0312606 A1 | 12/2008 | Harrison et al. |
| 2003/0093036 A1 | 5/2003 | Crossman et al. | | 2009/0054849 A1 | 2/2009 | Burnell et al. |
| 2003/0105430 A1 | 6/2003 | Lavi et al. | | 2009/0088688 A1 | 4/2009 | Timothy Donald et al. |
| 2003/0109833 A1 | 6/2003 | Sahpe | | 2010/0016793 A1 | 1/2010 | Jennings et al. |
| 2003/0120212 A1 | 6/2003 | Dedig et al. | | | | |
| 2003/0120222 A1 | 6/2003 | Vaillancourt | | FOREIGN PATENT DOCUMENTS | | |
| 2003/0121815 A1 | 7/2003 | Bergeron et al. | | CN | 2059579 U | 7/1990 |
| 2003/0135157 A1 | 7/2003 | Saulenas et al. | | CN | 1190599 A | 8/1998 |
| 2003/0181859 A1 | 9/2003 | Brunel | | CN | 1541121 A | 10/2004 |
| 2003/0184973 A1 | 10/2003 | Nagata et al. | | CN | 1550240 A | 12/2004 |
| 2003/0196928 A1 | 10/2003 | Parsons | | DE | 902776 C | 1/1954 |
| 2003/0199814 A1 | 10/2003 | Parsons et al. | | DE | 229932 A1 | 11/1985 |
| 2003/0208164 A1 | 11/2003 | Botich et al. | | DE | 3604826 A1 | 10/1986 |
| 2003/0212362 A1 | 11/2003 | Roser | | DE | 4428467 A1 | 2/1996 |
| 2003/0212370 A1 | 11/2003 | Barrelle | | DE | 29513214 U1 | 1/1997 |
| 2003/0212380 A1 | 11/2003 | Barrelle | | DE | 69506521 T2 | 6/1999 |
| 2003/0225368 A1 | 12/2003 | Landau et al. | | DE | 10207276 A1 | 9/2003 |
| 2003/0233070 A1 | 12/2003 | De La Serna et al. | | DE | 20311996 U1 | 10/2003 |
| 2003/0236502 A1 | 12/2003 | De La Serna et al. | | EP | 0111724 B1 | 11/1983 |
| 2003/0236504 A1 | 12/2003 | Chen | | EP | 0096314 A2 | 12/1983 |
| 2004/0015134 A1 | 1/2004 | Lavi et al. | | EP | 0144625 A2 | 6/1985 |
| 2004/0019326 A1 | 1/2004 | Gilbert et al. | | EP | 0240787 A2 | 3/1987 |
| 2004/0039336 A1 | 2/2004 | Amark et al. | | EP | 0516473 | 12/1992 |
| 2004/0039366 A1 | 2/2004 | MacLeod | | EP | 0331452 A2 | 8/1993 |
| 2004/0069044 A1 | 4/2004 | Lavi et al. | | EP | 0585626 A1 | 3/1994 |
| 2004/0087897 A1 | 5/2004 | Hjertman | | EP | 0389938 B1 | 5/1994 |
| 2004/0102740 A1 | 5/2004 | Meloul | | EP | 0482677 B1 | 4/1998 |
| 2004/0111054 A1 | 6/2004 | Landau et al. | | EP | 0602883 B1 | 7/1998 |
| 2004/0111057 A1 | 6/2004 | Wilkinson | | EP | 0857491 A1 | 8/1998 |
| 2004/0133159 A1 | 7/2004 | Haider et al. | | EP | 0824922 B1 | 4/2002 |
| 2004/0138618 A1 | 7/2004 | Mazzoni | | EP | 1260241 A1 | 11/2002 |
| 2004/0143224 A1 | 7/2004 | Field et al. | | EP | 0824923 B1 | 7/2003 |
| 2004/0153033 A1 | 8/2004 | Mazzoni | | EP | 1228777 B1 | 10/2003 |
| 2004/0225262 A1 | 11/2004 | Fathallah et al. | | EP | 0991441 B1 | 12/2003 |
| 2004/0243065 A1 | 12/2004 | McConnell et al. | | EP | 1166809 B1 | 3/2004 |
| 2005/0020979 A1 | 1/2005 | Westbye et al. | | EP | 0666084 B1 | 4/2004 |

| | | | | | | |
|---|---|---|---|---|---|---|
| EP | 0941133 | B1 | 4/2004 | WO | WO 88/10129 A1 | 12/1988 |
| EP | 1124601 | B1 | 12/2004 | WO | WO 92/19296 A | 11/1992 |
| EP | 1364667 | B1 | 4/2005 | WO | WO 93/02186 A1 | 2/1993 |
| EP | 1208858 | B1 | 6/2006 | WO | WO 93/21986 A2 | 11/1993 |
| EP | 1755710 | A1 | 2/2007 | WO | WO 93/23098 A1 | 11/1993 |
| EP | 1586341 | B1 | 1/2008 | WO | WO 94/04207 A1 | 3/1994 |
| EP | 1932558 | A1 | 6/2008 | WO | WO 94/07554 A1 | 4/1994 |
| EP | 2023980 | A1 | 2/2009 | WO | WO 94/11041 | 5/1994 |
| EP | 2129414 | A1 | 12/2009 | WO | WO 94/13342 A1 | 6/1994 |
| EP | 1755706 | B1 | 3/2010 | WO | WO 94/21316 A1 | 9/1994 |
| EP | 1928523 | B1 | 7/2010 | WO | WO 94/22511 A1 | 10/1994 |
| EP | 1518575 | B1 | 11/2010 | WO | WO 95/04562 A1 | 2/1995 |
| FR | 1014881 | A | 8/1952 | WO | WO 95/29720 A1 | 11/1995 |
| FR | 1169935 | A | 1/1959 | WO | WO 95/31235 A1 | 11/1995 |
| FR | 1538565 | A | 9/1968 | WO | WO 95/35126 A1 | 11/1995 |
| FR | 2506161 | A1 | 11/1982 | WO | WO 95/35126 A1 | 12/1995 |
| FR | 2629706 | A | 10/1989 | WO | 96/30065 A1 | 10/1996 |
| FR | 2654938 | A1 | 5/1991 | WO | WO 97/10865 A1 | 3/1997 |
| FR | 2665079 | A1 | 1/1992 | WO | WO 97/13538 A1 | 4/1997 |
| FR | 2717086 | A1 | 9/1995 | WO | WO 97/48430 A1 | 12/1997 |
| FR | 2741810 | A1 | 6/1997 | WO | WO 98/11927 A1 | 3/1998 |
| FR | 2861310 | A1 | 4/2005 | WO | WO 99/03529 A2 | 1/1999 |
| GB | 143084 | | 5/1920 | WO | WO 99/10030 A2 | 3/1999 |
| GB | 0412054 | | 6/1934 | WO | WO 99/22789 A1 | 5/1999 |
| GB | 728248 | | 4/1955 | WO | WO 99/37343 A | 7/1999 |
| GB | 909898 | | 11/1962 | WO | WO 99/53979 A1 | 10/1999 |
| GB | 1263355 | | 2/1972 | WO | WO 99/59658 A1 | 11/1999 |
| GB | 1311937 | A | 3/1973 | WO | WO 00/06227 A1 | 2/2000 |
| GB | 1514725 | | 6/1978 | WO | WO 00/07539 A1 | 2/2000 |
| GB | 2338033 | A | 12/1999 | WO | WO 00/13723 A2 | 3/2000 |
| GB | 2388033 | A | 11/2003 | WO | WO 00/24441 A1 | 5/2000 |
| GB | 2396298 | A | 6/2004 | WO | WO 00/35516 | 6/2000 |
| GB | 2396816 | A | 7/2004 | WO | WO 00/50107 A1 | 8/2000 |
| GB | 2397767 | A | 8/2004 | WO | WO 00/64515 A1 | 11/2000 |
| GB | 2414398 | A | 11/2005 | WO | WO 00/69488 A2 | 11/2000 |
| GB | 2414399 | A | 11/2005 | WO | WO 01/05456 A1 | 1/2001 |
| GB | 2414400 | A | 11/2005 | WO | 01/49347 A1 | 7/2001 |
| GB | 2414401 | A | 11/2005 | WO | WO 01/76666 A1 | 10/2001 |
| GB | 2414402 | A | 11/2005 | WO | WO 01/77384 A2 | 10/2001 |
| GB | 2414403 | A | 11/2005 | WO | WO 01/87384 A1 | 11/2001 |
| GB | 2424835 | A | 10/2006 | WO | WO 02/11799 A1 | 2/2002 |
| GB | 2424836 | A | 10/2006 | WO | WO 02/47746 A1 | 6/2002 |
| GB | 2424838 | A | 10/2006 | WO | WO 02/056947 A1 | 7/2002 |
| GB | 2433035 | A | 6/2007 | WO | WO 03/013632 A2 | 2/2003 |
| GB | 2437922 | A | 11/2007 | WO | WO 03/015853 | 2/2003 |
| GB | 2438591 | A | 12/2007 | WO | WO 03/039633 A2 | 5/2003 |
| GB | 2446778 | A | 8/2008 | WO | WO 03/047663 A2 | 6/2003 |
| JP | 59-115053 | A | 7/1984 | WO | WO 03/051434 A2 | 6/2003 |
| JP | 2-185261 | A | 7/1990 | WO | WO 03/066141 A1 | 8/2003 |
| JP | 2-502971 | T | 9/1990 | WO | WO 03/092771 | 11/2003 |
| JP | 11-501549 | T | 2/1992 | WO | WO 03/097133 | 11/2003 |
| JP | 5-161712 | A | 6/1993 | WO | WO 03/099358 A2 | 12/2003 |
| JP | 6-209996 | A | 8/1994 | WO | WO 2004/007554 A1 | 1/2004 |
| JP | 6-508773 | T | 10/1994 | WO | WO 2004/011065 A1 | 2/2004 |
| JP | 6-327770 | A | 11/1994 | WO | WO 2004/030732 A2 | 4/2004 |
| JP | 7-222799 | A | 8/1995 | WO | WO 2004/035117 A2 | 4/2004 |
| JP | 8-502180 | T | 3/1996 | WO | WO 2004/047890 A1 | 6/2004 |
| JP | 8-504354 | T | 5/1996 | WO | WO 2004/047891 A1 | 6/2004 |
| JP | 9-225029 | A | 9/1997 | WO | WO 2004/047892 A | 6/2004 |
| JP | 10-504474 | T | 5/1998 | WO | WO 2004/054644 A1 | 7/2004 |
| JP | 10-507935 | A | 8/1998 | WO | WO 2004/054645 A3 | 7/2004 |
| JP | 11-503637 | T | 3/1999 | WO | WO 2004/087242 A1 | 10/2004 |
| JP | 11-504536 | T | 4/1999 | WO | WO 2004/108194 A1 | 12/2004 |
| JP | 11-164887 | T | 6/1999 | WO | WO 2005/009515 A1 | 2/2005 |
| JP | 11-512332 | T | 10/1999 | WO | WO 2005/023341 A1 | 3/2005 |
| JP | 2000-510021 | T | 8/2000 | WO | WO 2005/025636 A2 | 3/2005 |
| JP | 2002-500933 | T | 1/2002 | WO | WO 2005/030301 A1 | 4/2005 |
| JP | 2002-095749 | A | 4/2002 | WO | WO 2005/035028 A1 | 4/2005 |
| JP | 2002-513547 | T | 5/2002 | WO | WO 2005/044345 A | 5/2005 |
| JP | 2002-526175 | A | 8/2002 | WO | WO 2005/044347 A1 | 5/2005 |
| JP | 2002-528182 | T | 9/2002 | WO | WO 2005/058396 | 6/2005 |
| JP | 2002-532161 | T | 10/2002 | WO | WO 2005/070481 A1 | 8/2005 |
| JP | 2003-511105 | T | 3/2003 | WO | WO 2005/082438 A1 | 9/2005 |
| JP | 2003-532500 | T | 11/2003 | WO | WO 2005/097238 A3 | 10/2005 |
| JP | 2003-533288 | A | 11/2003 | WO | WO 2005/115507 A1 | 12/2005 |
| JP | 2004-533282 | T | 11/2004 | WO | WO 2005/115508 A1 | 12/2005 |
| JP | 2004-33737 | A | 8/2005 | WO | WO 2005/115509 A1 | 12/2005 |
| NZ | 573171 | A | 11/2010 | WO | WO 2005/115510 A1 | 12/2005 |
| NZ | 573350 | A | 12/2010 | WO | WO 2005/115512 A1 | 12/2005 |

| | | |
|---|---|---|
| WO | WO 2005/115513 A1 | 12/2005 |
| WO | WO 2005/115514 A1 | 12/2005 |
| WO | WO 2005/120607 A2 | 12/2005 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.

* cited by examiner

INJECTION DEVICE

BACKGROUND TECHNOLOGY

The present invention relates to an injection device of the type that receives a syringe, extends it, discharges its contents and then retracts it automatically. Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring. The initial action of the drive spring is typically controlled by means of a trigger. Depression of the trigger causes the drive spring to become operative.

It is not uncommon for the operation of the trigger to be dependent upon the operation of a safety interlock, to prevent accidental operation. First the safety interlock must be operated, and then the trigger.

Market research has shown that it is beneficial for an injector device to provide some form of visual indication that the device is either ready to use or has been used. As ever, the simplest and cheapest way of achieving this is sought.

SUMMARY OF THE INVENTION

The injection devices of the present invention are designed to do this.

An injection device according to the present invention comprises:
  a housing adapted to receive a syringe having a discharge nozzle so that the syringe is movable between a retracted position in which the discharge nozzle is contained within the housing and an extended position in which the discharge nozzle extends from the housing;
  a drive that is acted upon and in turn acts upon the syringe;
  a trigger movable from a rest position, in which it causes the drive to be retained in a position corresponding to the retracted position of the syringe, to an active position, in which it no longer causes the drive to be so retained, thus allowing it to be advanced and in turn to advance the syringe from its retracted position to its extended position and discharge its contents through the discharge nozzle; and
  an interlock member movable between a locking position, at which it prevents movement of the trigger from its rest position to its active position, and a releasing position, at which it allows movement of the trigger from its rest position to its active position, the device having a visual indicator activating upon said trigger moving to an active position.

Thus, a device according to this invention provides a visual indication that it is either ready to use or has been used.

Preferably, the said visual indicator is provided by the trigger being retained in its active position. If such a device is ready for use, the trigger will be in its rest position. If it has been used, the trigger will be in its active position. These positions can be discriminated by the user. Moreover, the device incorporates the mechanism for achieving this result into a safety interlock mechanism, in the interests of simplicity. The trigger may comprise a locking member that, in the rest position of the trigger, engages a locking surface of the drive and, in the active position, does not.

The interlock member may comprises a primary member, the locking position of the interlock member being one in which the primary member projects from the discharge opening and the releasing position being one in which the primary member does not project from the discharge opening or projects from it to a lesser extent. This means that the interlock member may be moved from its locking position to its releasing position by bringing the end of the injection device into contact with the skin at the injection site. Apart from anything else, this ensures that the injection device is optimally positioned relative to the injection site before the injection cycle can begin. A primary member in the form of a sleeve allows a relatively large area to contact the skin and allows the discharge nozzle of the syringe to be advanced and retracted within it. In the case of a hypodermic syringe, the sleeve will shroud the needle from view, which is a good idea for the squeamish, particularly those who have to administer to themselves.

The locking of the trigger in its rest position may be achieved as follows. The trigger and the interlock member include a projection and an aperture, the projection being in register with the aperture when the interlock member is in its releasing position, but not otherwise. This allows the trigger to move from its rest position to its active position by movement of the projection into the aperture. The projection may be on the trigger and the aperture is in the interlock member.

The retention of the trigger in its active position may be achieved as follows. The trigger and another component of the device include a latching projection and a corresponding latching surface against which the latching projection latches when the trigger is in its active position. The latching projection may be on the trigger. This other component of the device is preferably the interlock member.

BRIEF DESCRIPTION OF THE DRAWINGS

The invention will now be described by way of example with reference to the accompanying drawings, in which.

DETAILED DESCRIPTION

Figure 1:
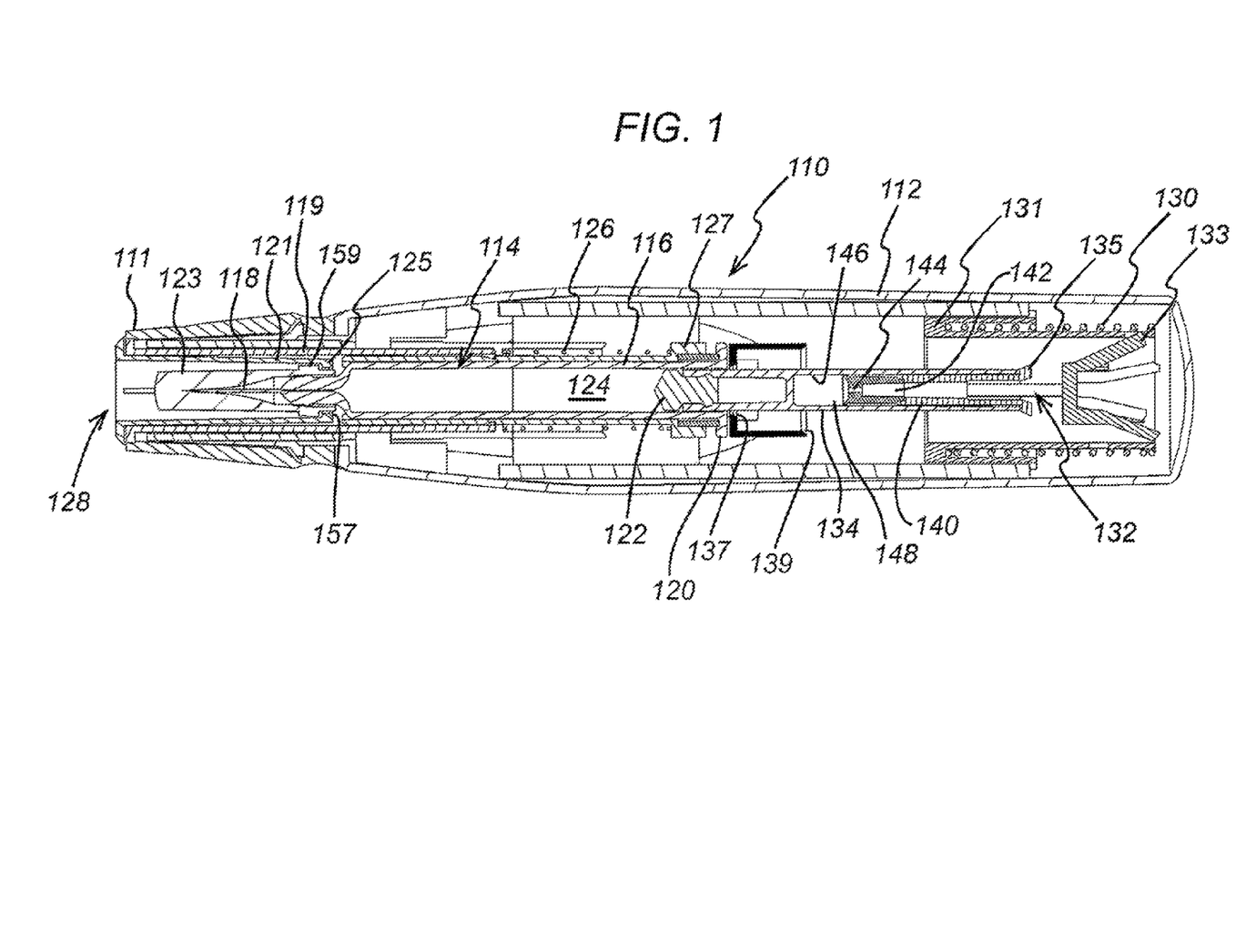
FIG. 1 shows in section an injection device of the type to which the present invention is applicable.

FIG. 1 shows an injection device 110 having a housing 112 that contains a hypodermic syringe 114 of conventional type, including a syringe body 116 terminating at one end in a hypodermic needle 118 and at the other in a flange 120. The conventional plunger that would normally be used to discharge the contents of the syringe 114 manually have been removed and replaced with a drive element 134, terminating in a bung 122. The bung 122 constrains a drug 124 to be administered within the syringe body 116. Whilst the syringe illustrated is of hypodermic type, this need not necessarily be so. Transcutaneous or ballistic dermal and subcutaneous syringes may also be used with the injection device of the present invention. As illustrated, the housing includes a return spring 126 that biases the syringe 114 from an extended position in which the needle 118 extends from an aperture 128 in the housing 112 to a retracted position in which the discharge nozzle 118 is contained within the housing 112. The return spring 126 acts on the syringe 114 via a syringe carrier 127.

At the other end of the housing is an actuator, which here takes the form of a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Hydrostatic forces acting through the drug and, to a lesser extent, static friction between the drive element 134 and the syringe body 116 initially ensure that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to flexible latch arms 133 on a first drive element 132. This in turn transmits drive via flexible latch arms 135 to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 defining a fluid reservoir 148, within which a damping fluid is contained.

A trigger (not shown) is provided that, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 32 and the first drive element 132 moves the second drive element 134, in each case by acting through the flexible latch arms 133, 135. The second drive element 134 moves and, by virtue of static friction and hydrostatic forces acting through the drug 124 to be administered, moves the syringe body 116 against the action of the return spring 126. The return spring 126 compresses and the hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic forces acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, the flexible latch arms 135 linking the first and second drive elements 132, 134 reach a constriction 137 within the housing 112. The constriction 137 moves the flexible latch arms 135 inwards from the position shown to a position at which they no longer couple the first drive element 136 to the second drive element 134, aided by the bevelled surfaces on the constriction 137. Once this happens, the first drive element 136 acts no longer on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. Thus, once the flexible latch arms 135 have been released, the force exerted by the drive spring 130 does work on the damping fluid, causing it to flow though the constriction formed by the vent 144 and also acts hydrostatically through the fluid and through friction between the first and second drive elements 132, 134, thence via the second drive element 134. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, the flexible latch arms 133 linking the drive sleeve 131 with the first drive element 132 reach another constriction 139 within the housing 112. The constriction 139 moves the flexible latch arms 133 inwards from the position shown to a position at which they no longer couple the drive sleeve 131 to the first drive element 132, aided by the bevelled surfaces on the constriction 139. Once this happens, the drive sleeve 131 acts no longer on the first drive element 132, allowing them to move relative each other. At this point, of course, the syringe 114 is released, because the forces developed by the drive spring 130 are no longer being transmitted to the syringe 114, and the only force acting on the syringe will be the return force from the return spring 126. Thus, the syringe 114 is now returned to its retracted position and the injection cycle is complete.

All this takes place, of course, only once the cap 111 has been removed from the end of the housing 112. As can be seen from FIG. 3, the end of the syringe is sealed with a boot 123. The central boss 121 of the cap that fits within the sleeve 119 when the cap 111 is installed on the housing 112, is hollow at the end and the lip 125 of the hollow end is bevelled on its leading edge 157, but not its trailing edge. Thus, as the cap 111 is installed, the leading edge 157 of the lip 125 rides over a shoulder 159 on the boot 123. However, as the cap 111 is removed, the trailing edge of the lip 125 will not ride over the shoulder 159, which means that the boot 123 is pulled off the syringe 114 as the cap 111 is removed.

Figure 2:
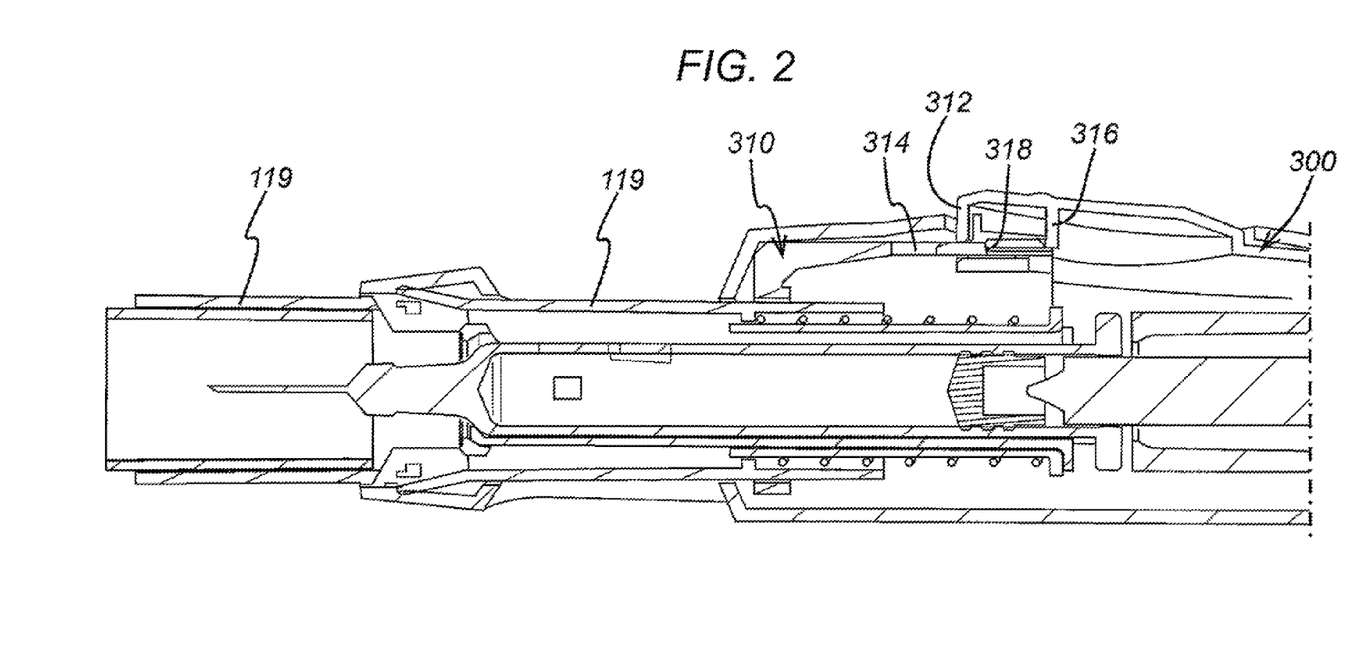
FIG. 2 shows in sectional schematic how that device may be modified in accordance with the invention.
Figure 3:
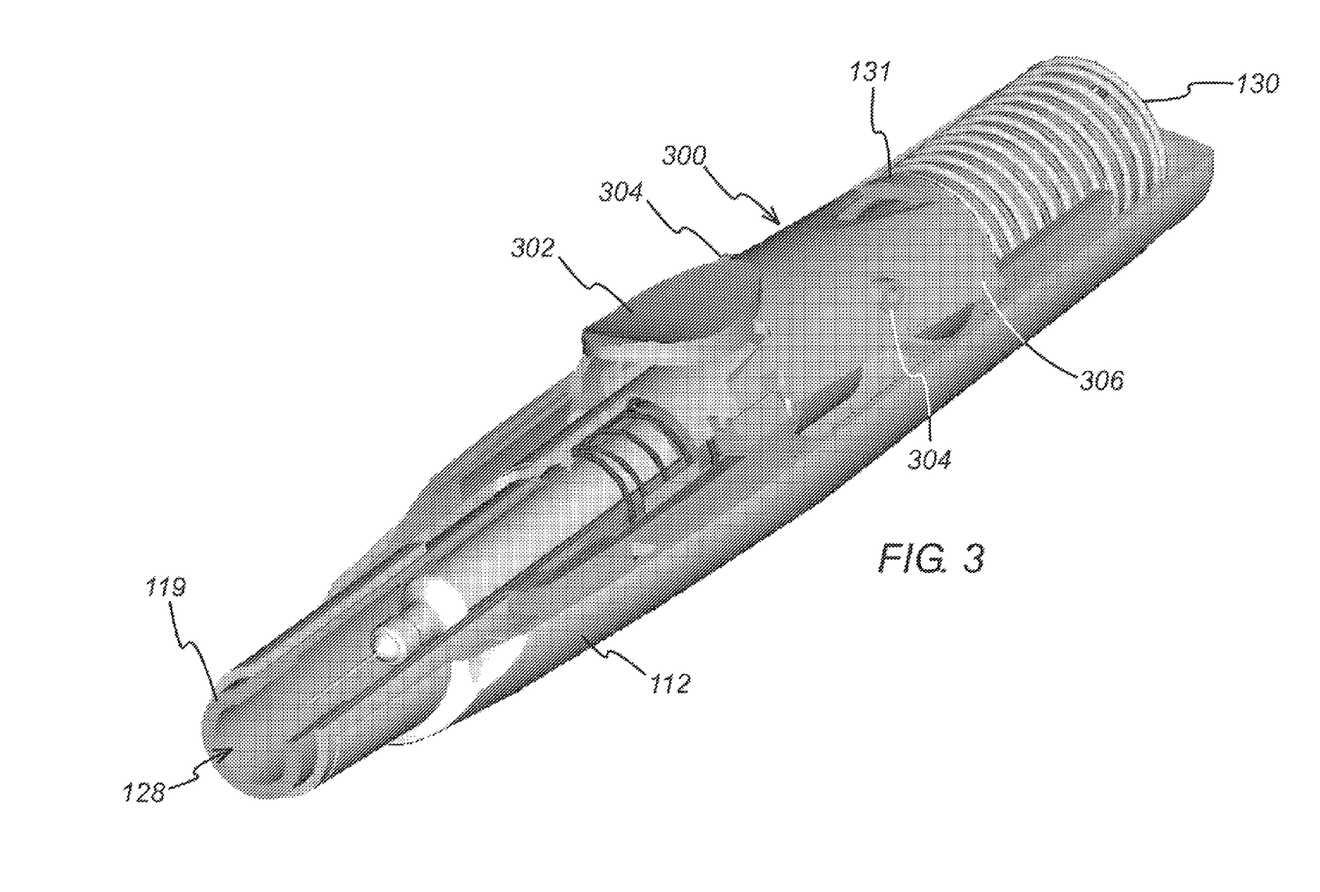
FIG. 3 is a cut-away view of the modified injection device.

FIGS. 2 and 3 show the device may be further modified. Although FIGS. 2 and 3 differ from FIG. 1 in some details, the principles now discussed are applicable to the device shown in FIG. 1. As can be seen, the device includes a trigger 300 having a button 302 at one end and a pair of lugs 304 that cooperate with pins (not shown) on the inside of the housing 112 to allow the trigger to pivot about an axis through the two lugs 304. The main body portion of the trigger 300, to which both the button 302 and the lugs 304 are affixed, forms a locking member 306. In the position shown, the end of the locking member 306 remote from the button 302 engages the end of the drive sleeve 131, against which the drive spring 130 acts and which in turn acts upon the multi-component drive previously discussed. This prevents the drive sleeve 131 from moving under the influence of the drive spring 130. When the button 302 is depressed, the trigger 300 pivots about the lugs 304, which lifts the end of the locking member 306 from its engagement with the drive sleeve 131, now allowing the drive sleeve 131 to move under the influence of the drive spring 130.

FIG. 3 shows the exit aperture 128 in the end of the housing 112, from which the end of the sleeve 119 can again be seen to emerge. As is shown in FIG. 2, the sleeve 119 is coupled to a button lock 310 which moves together with the sleeve 119. The trigger includes a stop pin 312 and the button lock 310 includes an stop aperture 314 which, as shown in FIG. 2, are out of register. They can, however, be brought into register by inward movement of the sleeve 119, which results in a corresponding movement of the button lock 310. Whilst the stop pin 312 and the stop aperture 314 are out of register, the button 302 may not be depressed; once they are in register, it may. The trigger 300 also includes a flexible, barbed latching projection 316 and the button lock 310 also includes a latching surface 318 with which the latching projection 316 engages when the button is depressed. Once the latching projection 316 has latched with the latching surface 318, the trigger 300 is permanently retained with the button 302 in its depressed position.

Thus, movement of the sleeve 119 in a direction into the housing 112, or in other words depression of the projecting end of the sleeve, brings the stop pin 312 into register with the stop aperture 314, allowing the trigger button 302 to be depressed, whereupon it is retained in its depressed position by the latching projection 316 and the latching surface 318. The sleeve 119 may be depressed by bringing the end of the injection device into contact with the skin at an injection site which, apart from anything else, ensures it is properly positioned before the injection cycle begins.

Figure 4:
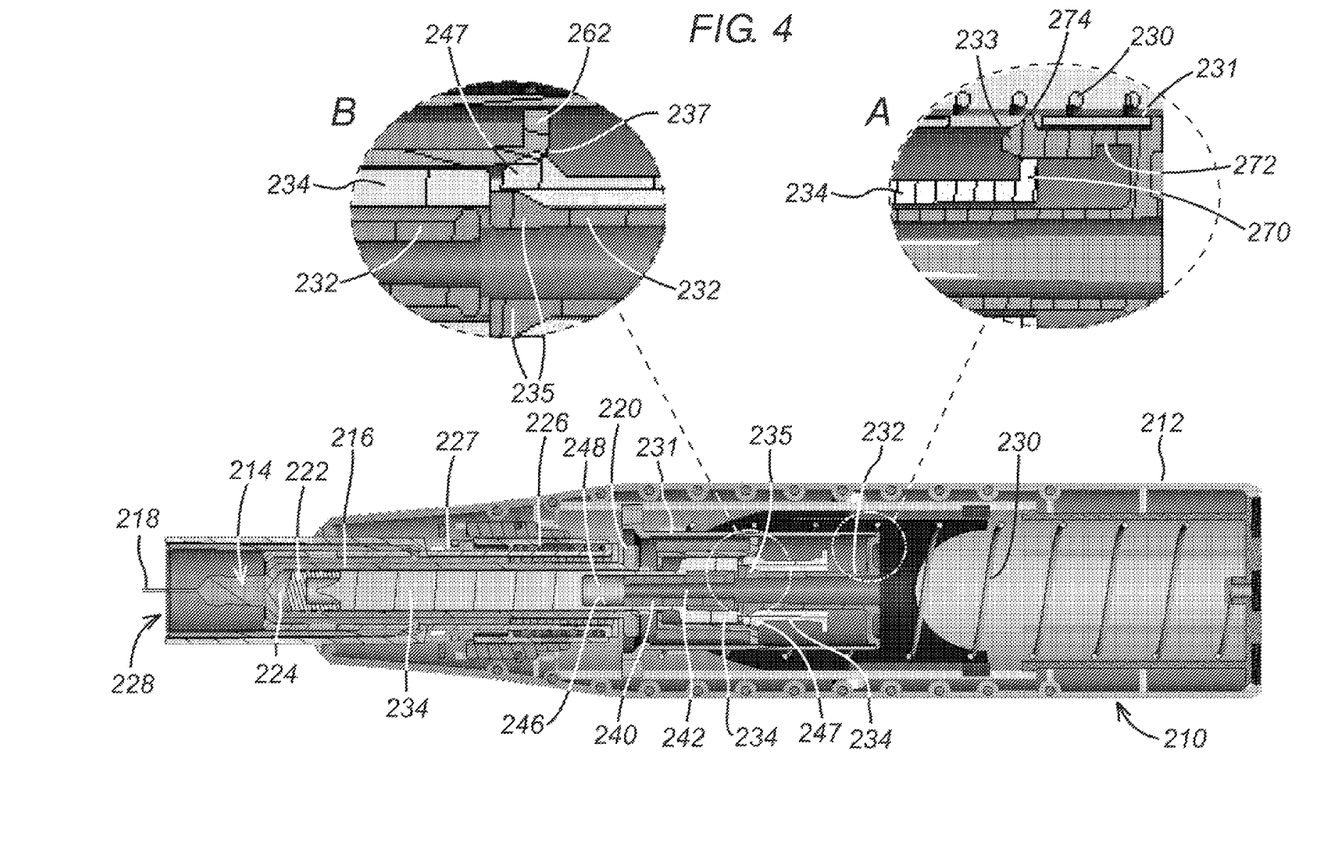
FIG. 4 shows in section a preferred injection device.

FIG. 4 shows a preferred injection device 210 to which the improvements described above with reference to FIGS. 2 and 3 are applied. Again, a housing 212 contains a hypodermic syringe 214. The syringe 214 is again of conventional type, including a syringe body 216 terminating at one end in a hypodermic needle 218 and at the other in a flange 220, and a rubber bung 222 that constraints a drug 224 to be administered within the syringe body 216. The conventional plunger that would normally be connected to the bung 222 and used to discharge the contents of the syringe 214 manually, has been removed and replaced with a multi-component drive element as will be described below. Whilst the syringe illustrated is again of hypodermic type, this need not necessarily be so. As illustrated, the housing includes a return spring 226 that biases the syringe 214 from an extended position in which the needle 218 extends from aperture 228 in the housing 212, to a retracted position in which the hypodermic needle 218 is contained within the housing 212. The return spring 226 acts on the syringe 214 via a sleeve 227.

At the other end of the housing is a compression drive spring 230. Drive from the drive spring 230 this transmitted via the multi-component drive to the syringe 214 to advance it from its retracted position to its extended position and discharge its contents through the needle 218. The drive accomplishes this task by acting directly on the drug 224 and the syringe 214. Hydrostatic forces acting through the drug 224 and, to a lesser extent, static friction between the bung 222 and the syringe body 216 initially ensure that they advance together, until the return spring 226 bottoms out or the syringe body 216 meets some other obstruction that retards its motion.

The multi component drive between the drive spring 230 and the syringe 214 again consists of three principal components. The drive sleeve 231 takes drive from the drive spring 230 and transmits it to flexible latch arms 233 on a first drive element 232. These elements are shown in detail "A". The first drive element 232 in turn transmits drive via flexible latch arms 235 to a second drive element 234. These elements are shown in detail "B". As before, the first drive element 232 includes a hollow stem 240, the inner cavity of which forms a collection chamber 242. The second drive element 234 includes a blind for 246 that is open at one end to receive the stem 240 and closed at the other. As can be seen, the bore 246 and the stem 240 define a fluid reservoir 248, within which a damping fluid is contained.

A trigger as described above with reference to FIGS. 6 and 7 is provided in the middle of the housing 212. The trigger, one operated, serves to decouple the drive sleeve 231 from the housing 212 allowing it to move relative to the housing 212 under the influence of the drive spring 230. The operation of the device is then as follows.

Initially, the drive spring 230 moves the drive sleeve 231, the drive sleeve 231 moves the first drive element 232 and the first drive element 232 moves the second drive element 234, in each case by acting through the flexible matching arms 233, 235. The second drive element 234 moves and, by virtue of static friction and hydrostatic forces acting through the drug 224 to be administered, moves the syringe body 216 against the action of the return spring 226. The return spring 226 compresses and the hypodermic needle 218 emerges from the exit aperture 228 of the housing 212. This continues until the return spring 226 bottoms out or the syringe body 216 meets some other obstruction that retards its motion. Because the static friction between the bung 222 and the syringe body 216 and the hydrostatic forces acting through the drug 224 to be administered are not sufficient to resist the full drive force developed by the drive spring 230, at this point the second drive element 234 begins to move within the syringe body 216 and the drug 224 begins to be discharged. Dynamic friction between the bung 222 and the syringe body 216 and hydrostatic forces acting through the drug 224 to be administered are, however, sufficient to retain the return spring 226 in its compressed state, so the hypodermic needle 218 remains extended.

Before the second drive element 234 reaches the end of its travel within the syringe body 216, so before the contents of the syringe have fully discharged, the flexible latch arms 235 linking the first and second drive elements 232, 234 reach a constriction 237. The constriction 237 is formed by a component 262 that is initially free to move relative to all other components, but that is constrained between the syringe flange 220 and additional flexible arms 247 on the second drive element 234. These additional flexible arms 247 overlie the flexible arms 235 on the first drive element 232, by means of which drive is transmitted to the second drive element 234. FIG. 3 illustrates the injection device 210 at the position where the additional flexible arms 247 are just making contact with the constriction 237 in the component 262.

The constriction 237 moves the additional flexible arms 247 inwards, aided by the bevelled surfaces on both, and the additional flexible arms 247 in turn move the flexible arms 235, by means of which drive is transmitted from the first drive element 232 to the second drive element 234, inwards from the position shown to a position at which they no longer couple the first and second drive elements together. Once this happens, the first drive element 232 acts no longer on the second drive element 234, allowing the first drive element 232 to move relative to the second drive element 234.

Because the damping fluid is contained within a reservoir 248 defined between the end of the first drive element 232 and the blind bore 246 in the second drive element 234, the volume of the reservoir 248 will tend to decrease as the first drive element 232 moves relative to the second drive element 234 when the former is acted upon by the drive spring 230. As the reservoir 248 collapses, damping fluid is forced into the collection chamber 242. Thus, once the flexible latch arms 235 have been released, the force exerted by the drive spring 230 does work on the damping fluid, causing it to flow into the collection chamber 242, and also acts hydrostatically through the fluid and through friction between the first and second drive elements 232, 234, thence via the second drive element 234. Losses associated with the flow of the damping fluid do not attenuate the force acting on the body of the syringe to a great extent. Thus, the return spring 226 remains compressed and the hypodermic needle remains extended.

After a time, the second drive element 234 completes its travel within the syringe body 216 and can go no further. At this point, the contents of the syringe 214 are completely discharged and the force exerted by the drive spring 230 acts to retain the second drive element 234 in its terminal position and to continue to cause the damping fluid to flow into the collection chamber 142, allowing the first drive element 232 to continue its movement.

A flange 270 on the rear of the second drive element 234 normally retains the flexible arms 233 in engagement with the drive sleeve 231. However, before the reservoir 248 of damping fluid is exhausted, the flexible latch arms 233 linking the drive sleeve 231 with the first drive element 232 move sufficiently far forward relative to the second drive element 234 that the flange 270 is brought to register with a rebate 272 in the flexible arms 233, whereupon it ceases to be effective in retaining the flexible arms 233 in engagement with the drive sleeve 231. Now, the drive sleeve 231 moves the flexible latch arms 233 inwards from the position shown to a position at which they no longer couple the drive sleeve 231 to the first drive element 232, aided by the bevelled latching surfaces 274 on the flexible arms 233. Once this happens, the drive sleeve 231 acts no longer on the first drive element 232, allowing them to move relative to each other. At this point, of course, the syringe 214 is released, because the forces developed by the drive spring 230 are no longer being transmitted to the syringe 214, and the only force acting on the syringe will be the return force from the return spring 226. Thus, the syringe 214 now returns to its retracted position and the injection cycle is complete.

The invention claimed is:
1. An injection device comprising:
a housing adapted to receive a syringe having a discharge nozzle;
a drive that is acted upon and in turn acts upon the syringe;
a trigger movable from a rest position, in which it causes the drive to be retained, to an active position, in which it no longer causes the drive to be so retained, thus allowing its contents to be discharged through the discharge nozzle; and
an interlock member movable between a locking position, at which it prevents movement of the trigger from its rest position to its active position, and a releasing position, at which it allows movement of the trigger from its rest position to its active position, the device having an indicator to show that it has been used provided by the trigger being retained in its active position and activating upon said trigger moving to an active position,
said injection device further includes a latching projection and a corresponding latching surface against which the latching projection latches when the trigger is in its active position, thereby retaining said trigger in a depressed position.

2. An injection device according to claim 1, in which the trigger comprises a locking member that, in the rest position of the trigger, engages a locking surface of the drive and, in the active position, does not.

3. An injection device according to claim 2 in which the interlock member comprises a primary member, the locking position of the interlock member is one in which the primary member projects from the discharge opening and the releasing position is one in which the primary member does not project from the discharge opening or projects from it to a lesser extent.

4. An injection device according to claim 2 in which the primary member is a sleeve.

5. An injection device according to claim 1 in which the interlock member comprises a projection and said injection device further including an aperture, the projection being in register with the aperture when the interlock member is in its releasing position, but not otherwise, thus allowing the trigger to move from its rest position to its active position by movement of the projection into the aperture.

6. An injection device according to claim 5 in which the projection is on the trigger and the aperture is in the interlock member.

7. An injection device according to claim 1 in which the latching projection is on the trigger.

* * * * *